United States Patent [19]
Talley

[11] Patent Number: 5,855,652
[45] Date of Patent: Jan. 5, 1999

[54] AEROSOL COLLECTOR AND CONCENTRATOR

[75] Inventor: Robert Talley, East Aurora, N.Y.

[73] Assignee: Topaz 2000, Inc., Amherst, N.Y.

[21] Appl. No.: 792,528

[22] Filed: Jan. 31, 1997

[51] Int. Cl.$^6$ ................................................. B03C 3/78
[52] U.S. Cl. ................. 96/44; 95/60; 95/75; 96/50; 96/63; 96/64; 96/228; 96/372
[58] Field of Search ................. 96/228, 233, 27, 96/44, 45, 50, 52, 53, 63, 64, 372, 374, 376, 377, 240; 95/58, 60, 68, 75, 196, 205, 281

[56] References Cited

U.S. PATENT DOCUMENTS

| | | | |
|---|---|---|---|
| 2,607,438 | 8/1952 | Bailey | 96/376 |
| 2,672,946 | 3/1954 | Rabkin et al. | 96/50 |
| 3,236,045 | 2/1966 | Berger et al. | 96/372 X |
| 3,600,817 | 8/1971 | Klein | 96/372 X |
| 3,958,958 | 5/1976 | Klugman et al. | 95/75 X |
| 3,960,505 | 6/1976 | Marks | 96/27 X |
| 4,222,748 | 9/1980 | Argo et al. | 96/233 X |
| 4,256,468 | 3/1981 | Mazer et al. | 96/44 X |
| 5,389,120 | 2/1995 | Sewell et al. | 96/233 |

OTHER PUBLICATIONS

Brian Cage, Keith Schreiber, Charles Barnes, and Jay Portnoy, "Evaluation of Four Bioaerosol Samplers in the Outdoor Environment," *Annals of Allergy*, 1995 (in press).

M.A. Chatigny, "Sampling Airborne Microorganisms," in *Air Sampling Instruments*, 5$^{th}$ed., (1978), American Conference of Government Ind. Hygienists, Cincinnati, OH, pp. E–1 to E–9.

A.A. Anderson, "New Sampler for the Collection, Sizing, and Enumeration of Viable Airborne Particles", *Journal of Bacteriology*, 76, 1958, pp. 471 to 484.

Andersen Microbial Air Samplers, Graseby Andersen, Smyrna, GA, Jan. 1994.

P.S. Brachman, et al., *Science*, 144, 1964, p. 1295.

Ace Glass, Inc., Vineland, NJ, General Price List, Jan. 1, 1995.

G.S. Rajhans, "Inertial, Gravitational and Diffusional Collectors," in *Air Sampling Instruments*, 5$^{th}$ed., (1978), American Conference of Government Ind. Hygienists, Cincinnati, OH, pp. 0–1 to 0–51.

(List continued on next page.)

*Primary Examiner*—Richard L. Chiesa
*Attorney, Agent, or Firm*—M. Lukacher

[57] ABSTRACT

Apparatus is disclosed for rapidly collecting aerosols containing solid particles and micro organisms, such as viruses and bacteria, from relatively large volumes of air and concentrating these particulates as samples in water. This apparatus operates under conditions conducive to preserving the integrity and viability of the collected micro organisms. Ambient air containing aerosols drawn into and through the collector's interior by an air mover, is mixed with very warm air saturated with moisture and then with cold air, to cause the resulting vapor mixture to become supersaturated. This supersaturated water vapor rapidly condenses onto the incoming aerosol particles to form droplets with particles at their centers. The airstream carrying these droplets enters a cloud of air ions produced by a corona generator or, alternately, by a radioactive source emitting alpha particles. The air ions transfer their charges to the droplets which are then attracted from the airstream to temporarily adhere to the collector screens which may carry a charge of polarity opposite of that imparted on the droplets or be grounded. The airstream then continues through the system and is vented. The particles collected on the screens are continuously or periodically washed off by a low volume flow or spray of water. The resulting highly concentrated particle suspension passes through a funnel and a peristaltic pump to an output port to yield time-sequential aliquots for external analysis. Using a multi-stage filtration and back flush process, additional particle size classification within aliquots is possible before analysis.

23 Claims, 4 Drawing Sheets

OTHER PUBLICATIONS

G.S. Rajhams, "Inertial and Gravitational Collectors," in *Air Sampling Instruments,* 6th ed., (1983), American Conference of Government Ind. Hygienists, Cincinnati, OH, pp. Q–1 to Q–40.

V.C. Furtado, "Air Movers and Samplers," in *Air Sampling Instruments,* 6th ed.., (1983) American Conference of Government Ind. Hygienists, Cincinnati, OH, pp. M1 to M–23.

D. L. Swift and M. Lippmann, "Electrostatic and Thermal Precipitators," in *Air Sampling Instruments,* 6th ed., (1983), American Conference of Government Ind. Hygienists, Cincinnati, OH, pp. R–1 to R–15.

E.L. Shipe, M.E. Tyler and D.N. Chapman, *Appl. Microbiology,* 7, 1959, pp. 349 to 354.

C.S. Cox, *The Aerobiological Pathway of Microorganisms,* John Wiley & Sons, Chichester, UK, 1987.

G.S. Rajhans, *op. cit.,* 1978.

C.S. Cox, *op. cit.,* 1987.

F. Errington and E.O. Powell, *J. Hyg.,* 67, 1969, pp. 387 to 399.

A. Ogawa, *Separation of Particles from Air and Gases,* vol. 11, CRC Press, Boca Raton, FL, 1984, pp. 1 to 49.

G.F. Leal Fereira, O.N. Oliveira, Jr., and J.A. Giacometti, *J. Appl. Phys,* 59,(9), 1986, pp. 3045–3049.

A. Ogawa, *op. cit.,* 1984.

D.L. Swift and M. Lippmann, *op. cit.,* 1983.

D.L. Swift and M. Lippmann, *ibid,* 1983.

AEROSOL COLLECTOR AND CONCENTRATOR

FIELD OF INVENTION

The present invention relates to system (method and apparatus) for capturing and concentrating in liquid airborne particles including microscopic organisms, while providing an apparatus configuration conducive to preservation of viability of the organisms.

This invention provides a reliable and effective process and an associated device to rapidly collect representative samples of airborne aerosols—in particular, aerosols containing biological particles, such as spores, bacteria, fungi, and viruses. The effectiveness of such a process depends both on the order and type of process steps utilized, as well as on the nature and details of a sampling device. In particular, the sampler needs to exhibit a high efficiency for collecting particles over a wide particle size range of about 0.02 to 40 $\mu$m, as well as to maintain viability of the collected microorganisms, concentrate all collected particles in a liquid medium (typically water), and quickly provide particle sample aliquots sequentially in time for subsequent particle identification and analysis.

BACKGROUND OF THE INVENTION

Currently, and in the recent past, numerous types of sampling devices have been advanced and are available for collection of airborne microorganisms (bioaerosols) from both outdoor and indoor environments. Each device has certain advantages and disadvantages, depending on the particular environment in which it is used and the type of sample to be collected. A reference list of recent comparative studies of bioaerosol sampling instruments (particularly for allergen collection) is provided in a recent article by Cage, et al.[1], which focuses on an evaluation of four bioaerosol samplers for use in outdoor environment. The samplers the authors compare include a Rotorod, a Kramer-Collins suction trap, an all-glass impinger (AGI-30), and the Spincon high-volume cyclonic liquid impinger. None of these samplers operates on a continuous or semi-continuous basis to provide samples for rapid or short-time analyses which are of considerable interest to the users.

The literature contains numerous other reviews of bio-aerosol samplers and collectors. Chatigny[2], for example, provides a rather full listing of commercially available devices most frequently used in sampling microbial aerosols of various types, sizes, and concentrations.

Both the Andersen multi-stage cascade impactor[3,4] and the AGI-30 all-glass impinger[5,6] have been recommended in the literature for use as laboratory standard samplers. The Andersen Viable Sampler is a well-known, six-stage, multi-orifice cascade impactor-type unit designed specifically for collection of airborne, viable bacteria on nutrient-filled Petri dishes. The resultant colonies can then be subjected to standard microbiological analyses.

The Andersen impactor can provide some direct classification of sizes in incoming particles, as the larger particles entering each successive stage cannot follow the air flow in jets directed at each nutrient treated impaction surface. Rather, the larger particles in each case impact on the surfaces, while the smaller ones pass onto the next stage designed to capture particles of smaller absolute size. The principal shortcoming of these (and typically other impactors, as well) is that the incoming particles are not collected in liquid and, therefore, the particles are subjected to considerable shock forces on impact, which may affect their viability. Further, the samples are not well suited to be subjected to subsequent manipulation that is often required to facilitate some of the instrumental bioparticle analysis techniques to be applied in a timely fashion. Two secondary weaknesses are that only relatively low intake air-flow rates (about 28 liters/min or less) are provided and there is no easy means to collect sequential samples to characterize particulates on a time-dependent basis.

The AGI-30 impinger, is an all-glass unit that operates by drawing aerosols through an inlet tube curved to simulate the human nasal passage. This tube forms all air-jet output. In operation, a one-half atmosphere vacuum is drawn across the jet tube so that a choked-flow condition is maintained, with a typical flow rate of about 12.5 l/min. This flow rate has been found to be useful for collecting microbial particles in the respirable size range of about 0.8 to 15 $\mu$m. The jet is directed into a collecting medium of water, typically about 20 ml in volume, but it can be smaller to achieve an increased concentration of microorganisms. The very low intake air flow rate can be a drawback in using this sampler, especially if very low concentrations of particulates in the outdoor environment need to be sampled in a short time frame of a few minutes. No known provision currently exists to operate this type of sampler on a continuous or semi-continuous basis to provide a sequence of collected samples to indicate relatively short-term behavior of an ambient outdoor aerosol.

In these samplers—as well as in a wide variety other collectors[7,8,9,10,11]—a primary concern has been to maintain the viability of the collected bioparticles. According to Cox[12], some attempts to develop improved impingers (in particular) that overcome such problems have been made by other workers, including Shipe[11], et al. and May, and these efforts have been at least partially successful. Cox notes (op. cit.) in the case of May's impinger "... the design represents a marked advance over more conventional impingers, but unfortunately, its complex construction in glass and ensuing cost represent disadvantages over classical impingers ...".

An additional shortcoming of the various impactors and impingers mentioned so far, is that neither continuous nor short-term integrated samples of the collected microorganisms are made readily available for further analysis. This shortcoming has been addressed, however, by the "sequential" and "tape" samplers. These include the Casella "Airborne Bacterial Sampler-MKII" and the New Brunswick "Microbiological Sampler."[13] These devices operate with a fixed narrow slit providing a particle-laden air jet of known velocity, which impacts on a nutrient agar-filled Petri dish that is mounted on a slowly rotating turntable. Following incubation, the exposed dishes permit colony counts to be made and correlated with time and sampling rate. A "Moving Slide" impactor from Meteorology Research, Inc., can deposit two samples from two identical slits onto a moving slide[14] for subsequent time and concentration analysis. These types of samplers show only limited capability to provide sequential samples suitable for timely instrumental analysis.

Errington and Powell[15] developed a cyclone sampler with an air-particle inlet into which was metered a low flow of suitable liquid that formed a thin liquid layer on the inside wall of the cyclone. The impacted particles on the cyclone wall were then carried by the liquid to the bottom of the unit. Typically, a cyclone collector can provide a somewhat milder stress environment on impacting particles than is usually available in a straight jet or virtual impactor systems[16,17]. This device is more effective with larger particles than with smaller ones.

Another technique explored and reported in the literature is the use of electrostatic-based samplers. Rather than using mechanical forces to separate the particles from the air stream, electrical forces are used; these electrical forces may provide further help in collecting the particles on some types of collection media. Typically, the charging of the particles to be sampled is done by passing the sample through the drift region of a high-voltage corona discharge. Either negative or positive coronas can be used, and the charges produced in the drift field are correspondingly also negative or positive[18]. Additional details of the utilization of coronas in charging aerosol particles to enhance particle collection are given by Ogawa[19], Lippmann[20], and Swift and Lippmann[21].

In the use of electrostatic precipitators for the collection of biological aerosols the effect, must be considered, which ultraviolet radiation, ozone, or nitrogen oxides, produced during corona generation, may have on the viability of the collected biological materials.

Despite the intense activity in the past to advance and develop bioaerosol samplers, a need remains for a bioaerosol collector that incorporates into a single device a number of features to achieve both improved process performance and greater overall capability than is exhibited by any of the instruments previously noted.

One of the problems with prior art devices mentioned above has been the inability to achieve high collection efficiencies of airborne microorganisms whose sizes are smaller than about 2 $\mu$m. Thus, the present invention has as a purpose to provide particle collection with a higher aerosol collection efficiency than with prior art devices, especially for submicron particles.

The second problem has been to be able to rapidly sample and process a sufficient volume of ambient air to ensure that a relatively large number of specific microorganisms of interest are collected (and ultimately concentrated) in a liquid to form a representative sample over a short time period of about two minutes or less. Increased sampling air flow in the collector and concentrator will be another purpose of this invention.

A third purpose will be to provide a continuous, uninterrupted sampling process to ensure that a time sequence of two minute samples over a much longer duration, suitably of the order of hours, will be available.

A fourth purpose will be to provide for partial or total separation of the particles collected, in liquid into one or more size classes to facilitate, the identification and analysis of particles of interest from the much larger total number of collected particles, which includes those representative of the natural ambient microorganisms.

A fifth purpose will be to concentrate the particles in each individual particle size range and thereby develop a time series of aliquots for further analysis of any microorganisms that might be present.

Finally, because many of the aerosol collectors tend to be unreliable and complex in their design, therefore expensive and difficult to operate, a sixth purpose will be to provide a collector/concentrator that will overcome these shortcomings.

SUMMARY, OBJECTS & FEATURES OF THE INVENTION

It is therefore one object of this invention to provide an improved electrostatic aerosol collector and concentrator ensuring a high volume sampling airflow.

It is another object of this invention to provide improved electrostatic aerosol collector and concentrator capable of concentrating airborne particles in water aliquots.

It is a further object of this invention to provide an improved electrostatic aerosol collector and concentrator that would be capable of high collection efficiencies particularly for particles smaller than 2 $\mu$m.

An additional object of this invention is to provide an improved electrostatic aerosol collector and concentrator capable of an operation over relatively long periods of time while allowing frequent aerosol samples of predetermined duration to be obtained.

Yet another object of this invention to is provide an improved electrostatic aerosol collector and concentrator which separates the sampled airborne particles in classes of sizes.

A further object of this invention is to provide an improved electrostatic aerosol collector and concentrator of a simplified construction.

Still an additional object of this invention is to provide an improved electrostatic aerosol collector and concentrator, protecting any biologically viable particles from the potentially harmful effects of electrostatic corona and/or ultraviolet radiation.

Briefly described, the collector apparatus, embodying the invention provides for collection of aerosols suspected of carrying harmful airborne particles including microorganisms, where need exists to carry out such collections efficiently in near real time to facilitate subsequent analysis and identification of, such particles including microorganisms.

The following features of this invention are intended to provide improved collection processes collector apparatus for aerosols in which:

High collection efficiency is ensured through increased continuous air flow and capture of solid airborne particles while preserving the viability of microorganisms part of said aerosols.

Electrostatic means is employed to increase collection efficiency of the airborne particles and to enable the use of liquid to remove solid particles collected on an uncharged or electrically charged screen to provide for subsequent analysis volumes of liquid in which said particles are concentrated. Alternately radioactive means is used to impart an electrical charge on the aerosol particles.

The capability is provided to capture and concentrate solid particles in the size range of 0.02 to 40 $\mu$m.

A relatively large volume of air moving relatively slowly through said apparatus is drawn for the purpose of increasing the number of solid particles collected in a given interval of time and for making samples of said particles available for subsequent analysis in a relatively short time, while minimizing any damage to microorganisms that could be caused through impact on the solid surfaces in said apparatus.

Airborne particles are electrically charged by passing the airflow containing said particles through a space charged cloud of air ions, said cloud produced by an electrical corona generator or, alternatively, by a small radioactive alpha particles source. The polarity of said charged cloud can be relatively frequently changed in order to avoid build up of electrical charges on the internal surfaces of said collector apparatus. The magnitude of the potential of said charged cloud is kept relatively low so as to minimize generation of ozone and ultraviolet radiation that could be harmful to said microorganisms. If a small radioactive source is employed to generate said cloud of charged air molecules, no significant ultraviolet radiation or ozone will be generated.

Moisture is introduced into the airflow at the inlet port in order to coat said solid particles with a layer of water in order to further protect any microorganisms contained in said airflow from harmful effects of any ozone or ultraviolet radiation that may have been generated during the operation.

The external hull is shaped like a cylinder, and an air mover, such as electrical fan is located in the circumferential center of said hull, said fan designed to draw air into said apparatus.

A cylindrically shaped screen is situated concentrically with the internal walls of said apparatus, said screen electrically charged to a potential of a polarity opposite that of said charged cloud and therefore that of the particles borne by the airflow through said apparatus. Said particles consequently are attracted to and adhere to said screen.

A relatively low volume flow of clean water is introduced to constantly wash said screens and thus removes and carries any particles that have been collected on said screens funnel located at the end of said apparatus, opposite the inlet port where water containing solid particles is collected. Said particle water containing particles is forced by a pump through tubing to a plurality of filters used to retain particles of certain size ranges.

Clean water flow is used at each stage of said filters to wash off and carry in a separate stream particles of a certain size range to a place where further analysis is carried out.

One field of applications for said apparatus would be during warfare or terrorist activities where the employment of biological agents is suspected. Another application could be hospitals to minimize the risk of airborne infections, especially in operating rooms.

The apparatus is essentially a hollow cylinder that has an electrically driven suction fan capable of forcing large volumes of ambient air at a relatively slow speed through the inside of the cylinder. As the particle bearing air enters the input port of the collector, it can be subjected to an externally generated warm, moist air stream, so as to increase the humidity of the incoming air flow. Next, a stream of externally generated cold air is introduced which causes rapid cooling of the particle bearing air flow and condensation of moisture on solid particles in said air flow, that act as condensation nuclei. The solid particles thus become each coated with a layer of water which tends to protect any microorganisms against detrimental effects of ozone, ultraviolet radiation, or of drying out.

Next the particle bearing air stream passes through a space cloud of air molecules electrically charged by corona generator or by said radioactive source. The charges are transferred to said particles.

Inside the apparatus there is a metallic screen situated concentrically with and close to the inside surface of the cylindrical hull of said apparatus. Said screen is electrically insulated from the grounded hull and is electrically charged to potential opposite that of said space cloud and of magnitude sufficient to attract and temporarily retain said charged particles which are solid particles enveloped in water layers and also water droplets. The charge polarity of said space cloud and said screen can change frequently so as to avoid a build up of electrical charges on the walls and other parts of the apparatus.

A low volume stream of water is directed at said screen and washes off the solid particles from it. The low voltage electrical charge on said screen is supplied from a low impedance source; consequently, the water stream washing said screen will not discharge it, because it will have a much higher impedance to ground.

The resulting aliquots with a high concentration of solid particles including microorganisms is collected by said funnel and forced through tubing by a pump, such as a peristalting pump, to enter a bank of serially arranged membrane filters, each said filter having progressively smaller pores. This arrangement of filters segregates said particles by size ranges. Particles of each size range greater than the size of the pores in a particular filter is retained in a space ahead of said filter and can be flushed out by suitably using a small volume of water or retained on said filter for subsequent analysis.

Microorganisms can be separated from other non-viable particles by culturing or by one of other methods that allow such separation in near real time. The separated microorganisms can then be identified and their relative concentration in the ambient air computed knowing the parameters of air and water flows.

BRIEF DESCRIPTION OF THE DRAWINGS

The present invention will be more fully understood with reference to the following detailed description thereof, when read in conjunction with the attached drawings, wherein like reference numbers refer to like parts and wherein.

DETAILED DESCRIPTION

Figure 1:
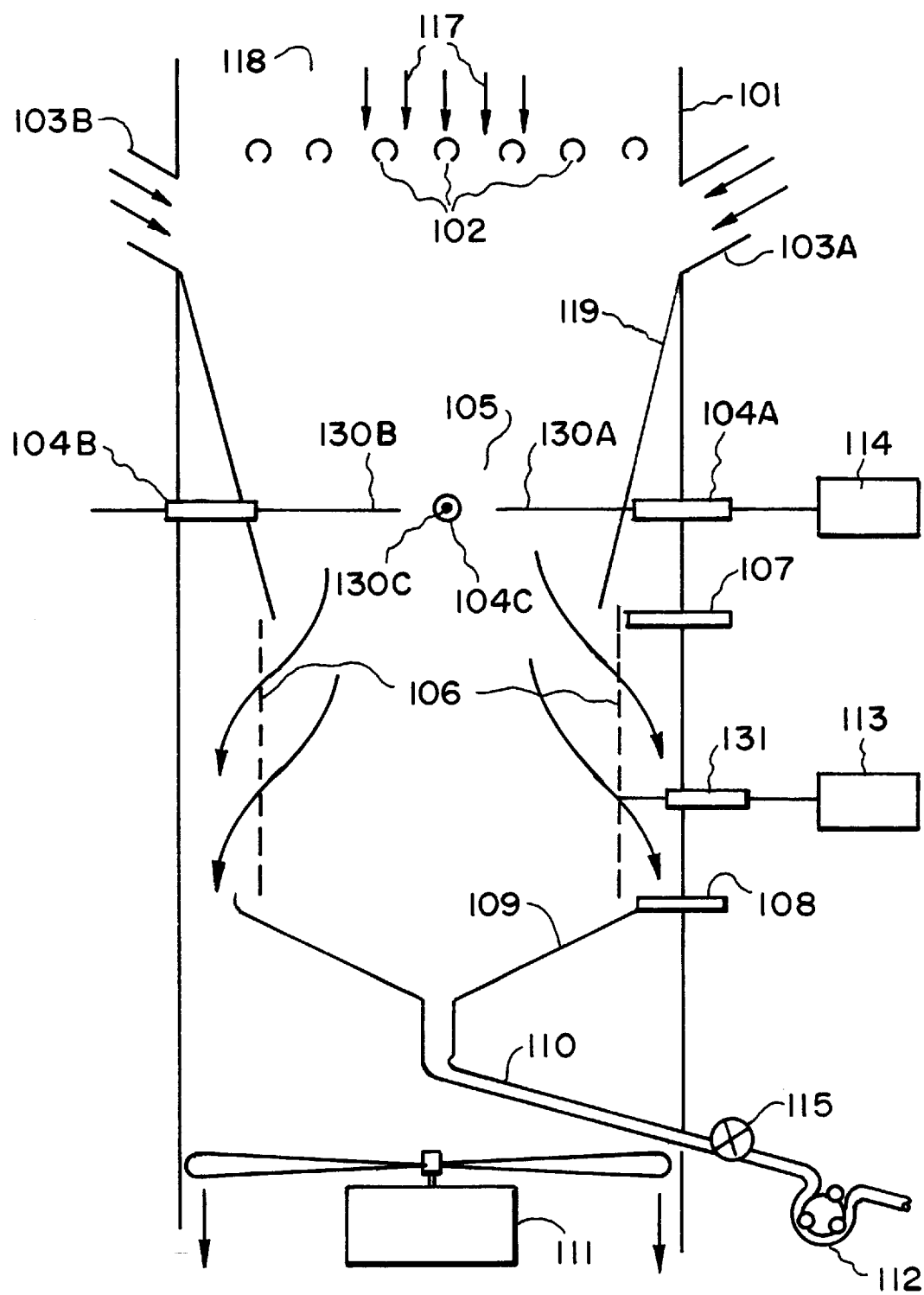
FIG. 1 is a schematic diagram schematically showing a cross-section of apparatus according to the invention.
Figure 2:
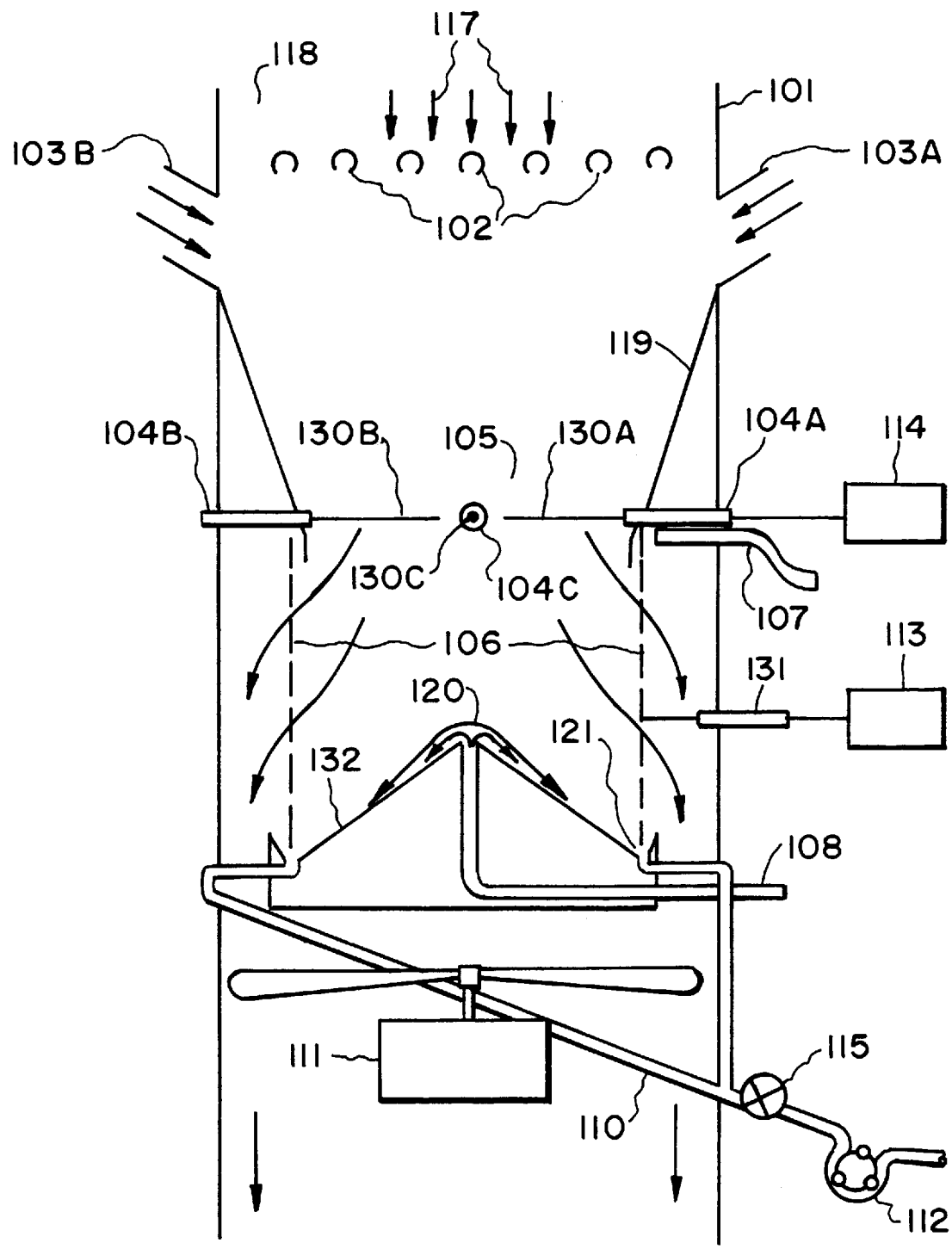
FIG. 2 is a diagram similar to the FIG. 1 which schematically depicts a cross-section of another embodiment of apparatus according to the invention.
Figure 3:
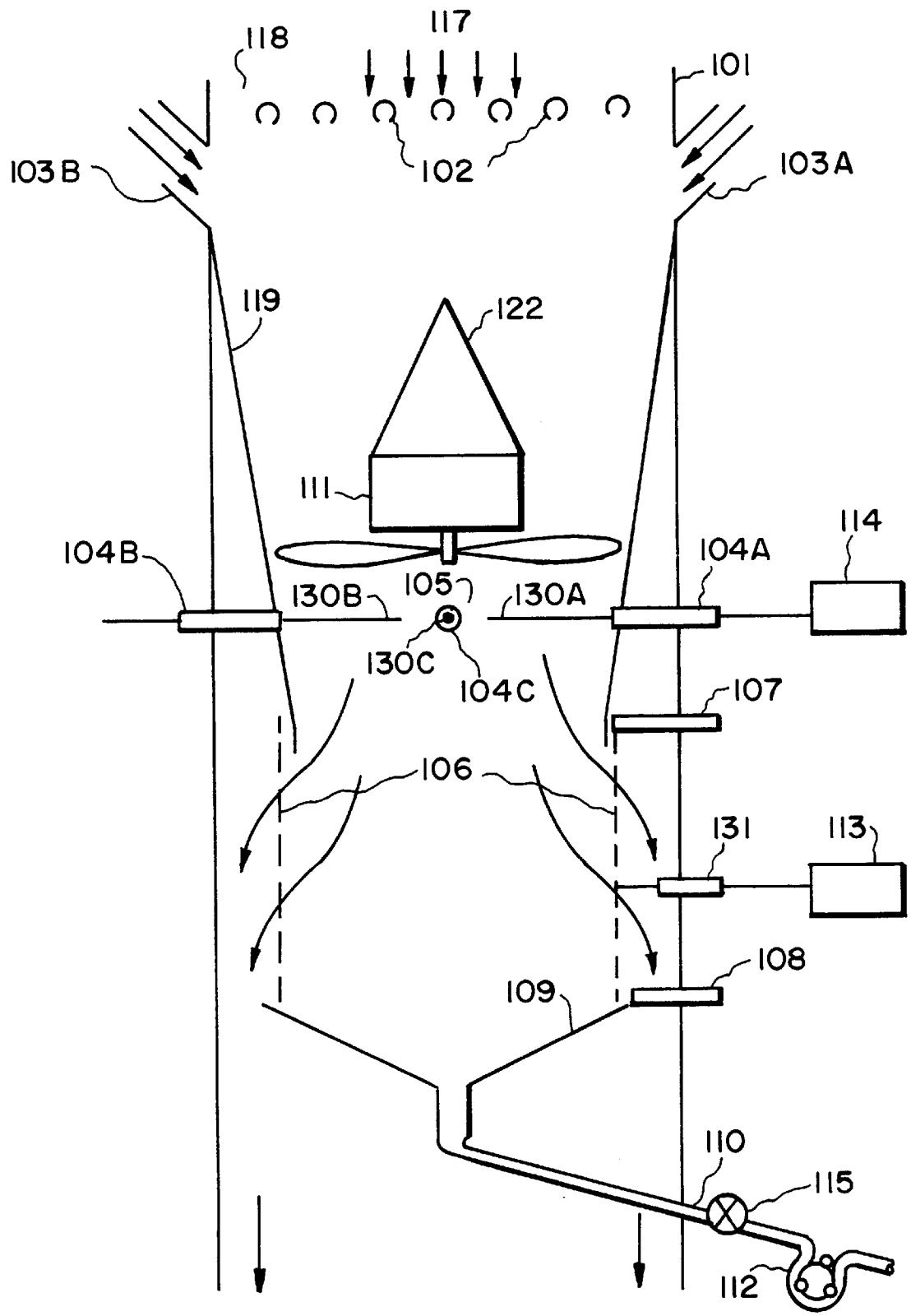
FIG. 3 is a diagram like FIGS. 1 and 2 which schematically illustrates a cross-section of yet another embodiment of apparatus according to the invention.
Figure 4:
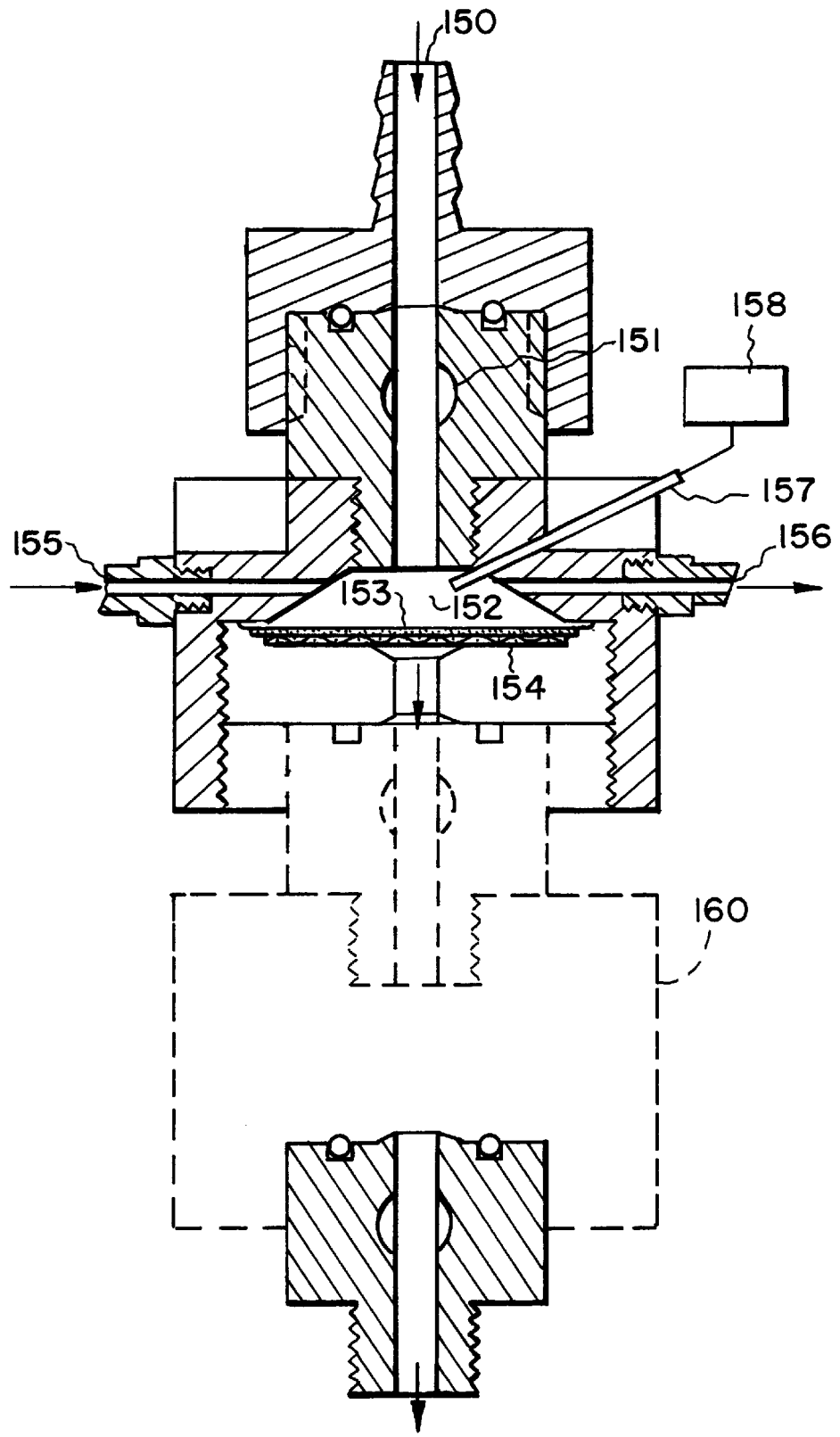
FIG. 4 is a schematic cross-section of a two-stage filter bank.

FIGS. 1, 2, and 3 schematically depict cross-sections of three versions of the apparatus subject of the present invention. There are structural and functional differences between the three the versions which are explained in the following.

FIG. 1 shows one embodiment of the invention. Ambient air 117 containing airborne particles enters the input port 118 of the apparatus. The air flow into the apparatus is achieved by the action of the motor-driven fan 111. The input flow is preferably laminar to avoid early air turbulence that might cause loss of particles due to undesirable deposition of the particles on the internal parts of the intake system of the apparatus. The length of input port 118 is short also to avoid particle loss.

The air flow into the interior of the apparatus passes a grid of perforated tubes 102 through which warm moist air is introduced into the air flow from an external source (not shown). The intent of this process is to raise the humidity and temperature levels of the air flow. Following the grid 102 cold air is introduced from another external source (not shown) through inlets 103A and 103B. The cold air causes the moisture to precipitate around the airborne particles forming thin water layers around the particles. The intent of this process is to protect any microorganisms being carried in the air flow from any harmful effect of ozone and/or ultraviolet radiation that could result from the action of the corona generator 114 used to electrically charge the air molecules in the air flow, and from drying out. The air flow is now directed by the structure 119 shaped like a truncated cone to the electrically charged space cloud 105 and from there to the electrically charged grid 106, the functions of which will become clear from the following.

The corona generator 114 through a plurality of electrodes 130A, 130 B and 130C which enter the interior of the collector/concentrator through insulating feed-throughs 104A, 104B and 104C, produces the electrically charged space cloud 105 of air molecules which in turn transfer their charges to the airborne particles.

An alternate way to charge the particles entering the apparatus is to employ a small commercially available, natural radioactive source that emits alpha particles. Such source could be using an isotope polonium-210 that emits 5.3 MeV α-particles having a penetration range in ambient air of about 3.7 cm; the α-particles have very low penetration power, they can be stopped with a sheet of paper. The α-particles when emitted into air strip electrons from air molecules along their path and thereby generate positive and negative free air ions in equal numbers that attach themselves to the passing aerosol particles charging them.

The air flow is now directed through the grid 106 toward the cylindrical walls 101 of the apparatus. The grid 106 is shaped like a cylinder and is concentric with the walls and is electrically charged to a potential of a polarity opposite that of the space cloud and therefore of the charged particles. The potential has magnitude just sufficient to attract and temporarily hold the charged particles. Furthermore, the electrical charge on the grid 106 is introduced and maintained by the low output impedance source 113. The grid 106 is charged through a lead passing through an insulating feed-through 131.

If the radioactive source is used to charge the aerosol particles, the grid 106 can be grounded, rather than charged to a potential as described above thus eliminating the need for the source 113. Furthermore, if the radioactive source is used, no ultraviolet radiation or ozone are generated, reducing the chance of adversely affecting any bioparticles. The need for the corona generator 114 is also eliminated as is the need for high voltage insulation and for safety devices to prevent shock to the operator of the apparatus.

A stream of water flows onto the grid 106 from the nozzle 107 and continuously flushes off the particles adhering to the grid 106. Since the electrical potential on the grid is relatively low and is maintained by the source 113 with a low output impedance, discharge of the potential from the grid is prevented because the electrical resistance of the stream of water is much higher than that of the source 113.

The stream of water after flushing the particles from the grid is collected by the funnel 109 and directed to the drain line 110. A swirling water flush is directed to the periphery of the funnel 109 by the nozzle 108 and prevents adhesion of the particles to the walls of the funnel.

The particle-bearing water flowing through the drain and the drain valve 115 is propelled by the peristalting pump 112 toward a single or a bank of filters (not shown here) of the type depicted in FIG. 4.

FIG. 2 illustrates schematically the cross-section of an alternative configuration of the apparatus. As is apparent from this FIG., the main difference of this configuration vs. the one of FIG. 1 is the means 132 for collecting the water that has flushed the grid 106. Instead of a funnel as in FIG. 1, the means 132 is in shape of an inverted cone with the stream of flushing water being introduced through the centrally located opening 120. The water is collected in the circular trough 121 and flows from there through the drain 110 and drain valve 115 to the peristalting pump 112.

FIG. 3 shows schematically the cross-section of yet another configuration of the apparatus. This configuration is similar to that of FIG. 1, except for the location and the orientation of the fan. Cone 122 protects the fan and directs the airflow. In this position the fan will cause temporary increase in air speed and some turbulence to provide better mixing of particles in the air flow, water condensation, and more complete charging of the solid particles due to interaction with air ions in the space charge cloud.

The particle-bearing aliquot is passed by the action of the peristalting pump to the output port of the apparatus, where the particles can be extracted using filters. In addition, it is possible to sort these particles by size using a bank of a plurality of filters each the filter having pores smaller than those of the preceding filter. In this manner particles greater than the pore size of the downstream filter are collected on the filter or in a space in front of the filter.

FIG. 4 shows a cross-section of a two stage bank of filters in which the first stage is shown in greater detail.

Particle-bearing water enters the filter bank through the input port 150, passes through the input shut-off valve 151 into pre-filter space 152, then through the filter 153 and the supporting screen 154 to the outlet port of the first filter stage, from which point the particle-bearing water enters the second filter stage.

Particles greater than the pore size of the filter 153 either adhere to the surface of the filter or remain in the pre-filter space 152. These particles can be removed for further analysis by passing filtered water through the inlet 155 into the pre-filter space and then out through the outlet 156. To dislodge the particles adhering to the surface of the first filter 153 and return them to the aliquot in the pre-filter space 152, an ultrasonic agitating means consisting of the ultrasonic driver 158 and the probe 157 is used.

The second stage 160 of the filter bank is identical to the first stage is indicated by its outline only.

The microorganisms in the aliquots emerging from the pre-filter spaces 152 of the filter bank can be isolated from non-viable solid particles and identified by culturing, mass spectrometry, spectroscopy, ultracentrifuge separation, immunoassays, gene probes, or other means.

It is to be understood that the preceding descriptions are illustrative only and that changes can be made in the aerosol collector/concentrator apparatus, subject of the invention, its components, materials, and elements, the sequences of operations and process steps, as well as in all other aspects of this invention discussed herein without departing from the scope of this invention.

REFERENCES:

1. Brian Cage, Keith Schreiber, Charles Barnes, and Jay Portnoy, "Evaluation of Four Bioaerosol Samplers in the Outdoor Environment, *Annals of Allergy,* 1995 (in press)
2. M. A. Chatigny, "Sampling Airborne Microorganisms," in *Air Sampling Instruments,* 5$^{th}$ ed., (1978), American Conference of Government Ind. Hygienist, Cincinnati, Ohio, pp. E1–E10
3. A. A. Andersen, "New Sampler for the Collection, Sizing, and Enumeration of Viable Airborne Particles", *Journal of Bacteriology,* 76, 1958, pp. 471–484
4. Andersen Microbial Air Samplers, Graseby Andersen, Smyrna, Ga.
5. P. S. Brachman, et al., *Science,* 144, 1964, pp. 1295
6. Ace Glass, Inc., Vineland, N.J.
7. G. S. Rajhans, "Inertial and Gravitational Collectors," in *Air Sampling Instruments,* 5$^{th}$ ed., (1978), American Conference of Government Ind. Hygienist, Cincinnati, Ohio, pp. O–1 to O–51
8. G. S. Rajhans, "Inertial and Gravitational Collectors," in *Air Sampling Instruments,* 6$^{th}$ ed., (1983), American Conference of Government Ind. Hygienist, Cincinnati, Ohio, pp. Q-1
9. V. C. Furtado, "Air Movers and Samplers," American Conference of Government Ind. Hygienist, Cincinnati, Ohio, 6th ed., (1983), pp. M1–M23
10. D. L. Swift and M. Lippmann, "Electrostatic and Thermal Precipitators in *Air Sampling Instruments,* 6$^{th}$ ed., (1983) American Conference of Government Ind. Hygienists, Cincinnati, Ohio, pp. R-1 to R 15

11. E. L. Shipe, M. E. Tyler and D. N. Chapman, *Appl. Microbiology,* 7, 349–354 (1959)

12. C. S. Cox, *The Aerobiological Pathway of Microorganisms,* John Wiley & Sons, Chichester, UK, 1987

13. G. S. Rajhans, ibid., 1978

14. C. S. Cox, ibid., 1987

15. F. Errington and E. O. Powell, *J. Hyg.,* 67, 387–399, (1969)

16. C. S. Cox. ibid., 1987

17. A. Ogawa, Separation of Particles from Air and Gases, Vol. 11, CRC Press, Boca Raton, Fla., 1984, pp. 1–49

18. G. F. Leal Fereira, O. N. Oliveira, Jr., and J. A. Giacometti, J. Appl. Phys, 59,(9), 3045–3049 (1986)

19. A. Ogawa, ibid. 1984

20. M. Lippmann, "Electrostatic Precipitators," in *Air Sampling Instruments,* $5^{th}$ ed. (1978), American Conference of Government Ind. Hygienists, Cincinnati, Ohio, pp. P–1 to P–20

21. D. L. Swift and M. Lippmann, "Electrostatic and Thermal Precipitators," in *Air Sampling Instruments,* $6^{th}$ ed. (1983), American Conference of Government Ind. Hygienists, Cincinnati, Ohio, pp. R–1 to R–15

I claim:

1. Aerosol collector/concentrator comprising a cylindrically shaped body; the body having an entrance and an exit port of air; an axially situated within said body and electrically driven air mover to impel and move ambient air through said body; means for introducing moisture into the impelled air and raise the temperature of the air; means to introduce cooled air into incoming air to precipitate formation of water droplets on any solid particles being carried by the air; a collector structure situated within said body disposed to intercept said air flow, said collector structure designed to collect any solid particles from the air and temporarily retain them; and a water flow dispenser which continuously flushes the retained solid particles from said structure; and means to collect said water containing solid particles.

2. Apparatus per claim 1 further comprising electrical means to generate an electrostatically charged cloud of air molecules within said body intercepting the flow of air through the body; in which said collector structure is situated concentrically with the walls of said body and relatively close to said walls said structure electrically charged to a potential with polarity opposite of the polarity of said charged cloud.

3. Apparatus per claim 2 in which the electrical means includes a plurality of peripherally situated electrodes protruding into the body, the electrodes generating a corona discharge within the body.

4. Apparatus per claim 2 wherein the structure situated concentrically with the walls is electrically charged to a relatively low potential from a source of a low impedance.

5. Apparatus per claim 1 in which the air mover is located in a relatively close proximity to the exit port, said air mover having blades facing toward the entrance port.

6. Apparatus per claim 5 in which a cone structure is mounted on the electric motor of said air mover, said cone structure designed to direct said air flow.

7. Apparatus per claim 1 in which said water collecting means has a funnel shape.

8. Apparatus per claim 1 in which said water collecting means is axially located within said body and between the entrance port and the air mover.

9. Apparatus per claim 1 further comprising means for introducing water flow to wash off any particles adhering to the surface of the water collecting means.

10. Apparatus per claim 9 wherein the water containing particles is collected by a circular trough situated concentrically at the base of an inverted cone.

11. Apparatus per claim 1 in which said water collecting means has a shape of an inverted cone with its apex facing in a direction opposite to the direction of the air flowing through the body.

12. Apparatus per claim 11 wherein the water collecting means has an opening centrally located in said apex, said opening designed to allow water to flow through it, and said water to wash off any particles adhering to the surface of the water collecting means.

13. Apparatus per claim 1 wherein the charged cloud is generated by using a radioactive emitter of alpha particles.

14. Apparatus per claim 1 wherein the means for introducing moisture and the means for introducing cooled air are located within the body in relatively close proximity to the entrance port.

15. Apparatus per claim 1 wherein the collector structure is grounded to the body of said apparatus.

16. Apparatus per claim 1 further comprising a pump, and a tube to carry said water to the pump.

17. Apparatus per claim 16 wherein the pump is a peristaltic pump.

18. Apparatus per claim 1 wherein the particle carrying water is propelled by a pump to a bank of filters.

19. Apparatus per claim 18, wherein the bank of filters comprises a plurality of stages, each stage designed to progressively retain particles of size greater than a size predetermined for each stage.

20. Apparatus per claim 19, wherein water flow means is incorporated in each stage to remove the retained particles from said body and to transport them outside said body for analysis.

21. Apparatus per claim 1, wherein said collector structure is situated normal to the direction of said air flow.

22. Apparatus per claim 1, wherein said collector structure is situated at an angle to the direction of said air flow.

23. Apparatus per claim 1 designed to implement the following sequence of operations:

ambient air is drawn into the apparatus by the action of said air mover;

said ambient air is exposed to a hot air stream saturated with moisture;

the moisturized and heated air is mixed with a much cooler air causing the moisture to be supersaturated and to condense on the aerosol particles in the air, forming droplets;

the condensed moisture absorbed to the surface of each particle forms a liquid sheath around each particle, said sheath protecting the particle against the damaging effects of ozone, UV, drying out, and mechanical damage;

said formation of droplets also effectively generates larger exterior area for each particle facilitating acquisition of electrical charges and therefore subsequent collection of said particles;

said electrical charges are generated either by a corona discharge means or by a radioactive source of alpha particles;

said charged droplets containing particles are collected on said collector structure that intercepts the air flow;

the particles adhering to said collector structure are washed off with small volumes of water into said collecting means from which aliquots for analysis can be obtained.

* * * * *